United States Patent
McNeil-Watson (10) Patent No.: US 8,573,404 B2
(45) Date of Patent: Nov. 5, 2013

(54) CONTINUOUS PARTICLE AND MACRO-MOLECULAR ZETA POTENTIAL MEASUREMENTS USING FIELD FLOW FRACTIONATION COMBINED MICRO-ELECTROPHORESIS

(75) Inventor: Fraser McNeil-Watson, Malvern (GB)

(73) Assignee: Malvern Instruments, Ltd., Malvern (GB)

( * ) Notice: Subject to any disclaimer, the term of this patent is extended or adjusted under 35 U.S.C. 154(b) by 55 days.

(21) Appl. No.: 12/972,318

(22) Filed: Dec. 17, 2010

(65) Prior Publication Data

US 2011/0155650 A1 Jun. 30, 2011

Related U.S. Application Data

(60) Provisional application No. 61/287,285, filed on Dec. 17, 2009.

(51) Int. Cl.
*B03B 5/00* (2006.01)
(52) U.S. Cl.
USPC .............. 209/155; 209/455; 356/39; 356/73; 210/634; 210/637
(58) Field of Classification Search
USPC ................. 209/155; 210/22, 23, 101
See application file for complete search history.

(56) References Cited

U.S. PATENT DOCUMENTS

| | | | | | |
|---|---|---|---|---|---|
| 4,147,621 | A | * | 4/1979 | Giddings | 210/637 |
| 5,112,782 | A | * | 5/1992 | Brown et al. | 501/144 |
| 5,971,158 | A | * | 10/1999 | Yager et al. | 209/155 |
| 6,365,050 | B1 | * | 4/2002 | Cauchon | 210/635 |
| 6,568,245 | B2 | * | 5/2003 | Kaufman | 73/28.02 |
| 6,695,147 | B1 | * | 2/2004 | Yager et al. | 209/455 |
| 7,262,838 | B2 | * | 8/2007 | Fritz | 356/73 |
| 7,688,427 | B2 | * | 3/2010 | Cox et al. | 356/39 |
| 2004/0000519 | A1 | * | 1/2004 | Jiang et al. | 210/634 |

* cited by examiner

*Primary Examiner* — Terrell Matthews
(74) *Attorney, Agent, or Firm* — Kristofer E. Elbing (57) ABSTRACT

In one general aspect, an instrument for measuring characteristics of particles suspended in a fluid is disclosed. It includes a closed wall surface defining a fractionation channel having a input opening, an output opening, and a flow axis that spans downstream from the input opening for the channel to the output opening. A force application subsystem has a force application output oriented perpendicular to at least part of the flow axis of the fractionation channel. A particle characteristic measurement subsystem is located hydraulically downstream from at least a portion of the closed wall surface defining the fractionation channel, and includes a sensor positioned to sense a property of the suspended particles in the potential measurement subsystem as well as a signal output responsive to the sensor. A result processor has a signal input responsive to the signal output of the particle characteristic measurement subsystem, zeta potential processing logic responsive to the particle characteristic measurement subsystem, and a particle characteristic signal output responsive to the particle characteristic processing logic.

15 Claims, 6 Drawing Sheets

CONTINUOUS PARTICLE AND MACRO-MOLECULAR ZETA POTENTIAL MEASUREMENTS USING FIELD FLOW FRACTIONATION COMBINED MICRO-ELECTROPHORESIS

CROSS-REFERENCE TO RELATED APPLICATION

This application claims the benefit of U.S. Provisional Application No. 61/287,285, filed Dec. 17, 2009, which is herein incorporated by reference.

FIELD OF THE INVENTION

This invention relates to methods and apparatus for detecting properties of suspended particles.

BACKGROUND OF THE INVENTION

Field flow fractionation (FFF) is known in a variety of implementations to separate populations of macromolecules or nanoparticles (colloidal particles) in a range of sizes from about 0.5 nm to a few microns into subranges of particle size to enable more accurate determination of particle size distribution. FFF is described in more detail in U.S. Pat. No. 4,147,621, granted Apr. 3, 1979, entitled "Method and Apparatus for Flow Field-Flow Fractionation," issued to John C. Giddings, and herein incorporated by reference. Many detection methods respond more readily to large particles than small (or vice versa) so improved quantification is possible if a sample that is mixed (heterogeneous) in size can be fractionated.

It is particularly convenient if this can be done continuously and FFF methods do this for a wider range of sizes in the range mentioned, and more rapidly and effectively than some other methods such as the use of a size exclusion chromatography column.

In general an FFF technique consists in flowing a suspension of particles axially through a small channel, which can be a fraction of a millimeter in depth, a few millimeters wide, and a few centimeters long, with a force applied at right angles to the flow. We will consider this to be in a vertical direction but the orientation is usually not important. The force can arise in a variety of ways, and we will consider cross flow (XF FFF, XF4) to be the method of choice, but gravitation and temperature among others have been used.

Figure 7:
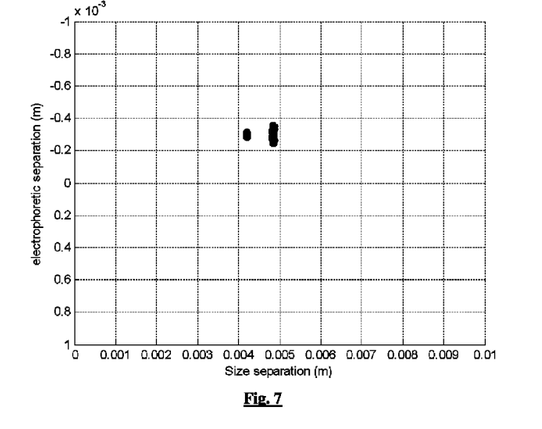
FIG. 7 is an illustrative plot of mobility against size for model 10 and 100 nm particles with a same mobility.
Figure 8:
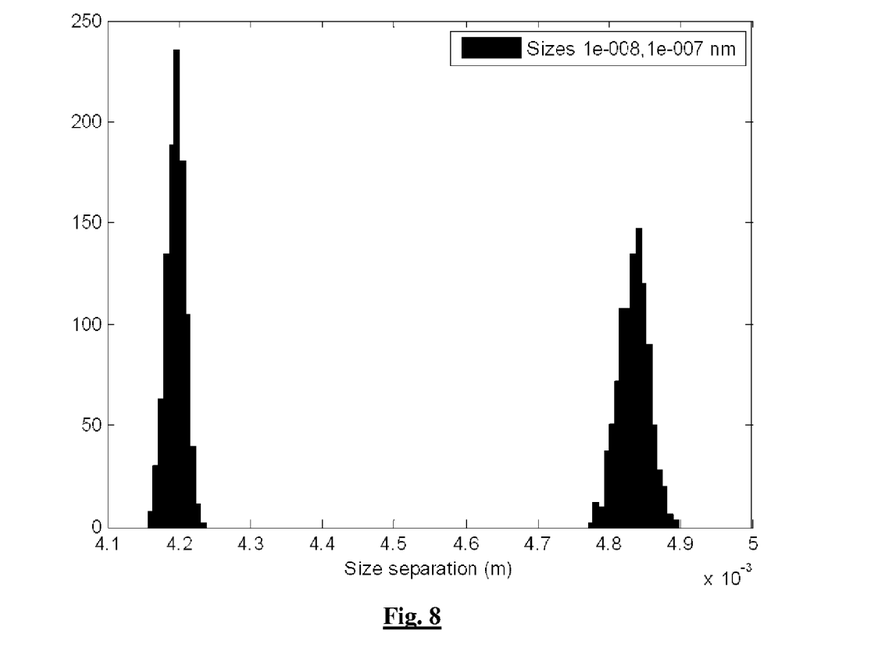
FIG. 8 is an illustrative size separation histogram for the model 10 and 100 nm particles with the same mobility.
Figure 9:
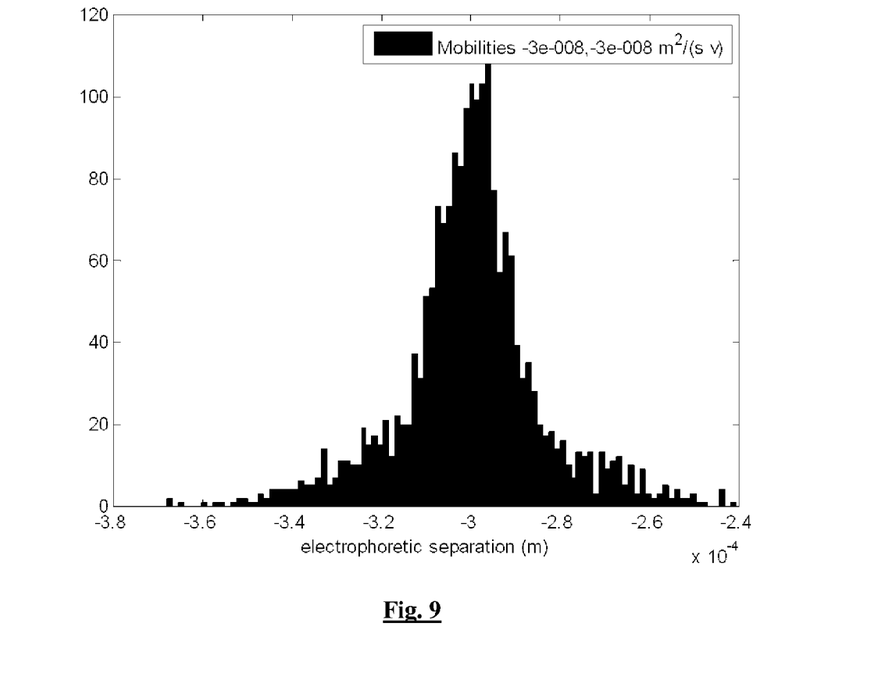
FIG. 9 is a second illustrative size separation histogram for model that cannot be distinguished based on zeta analysis alone.
Figure 10:
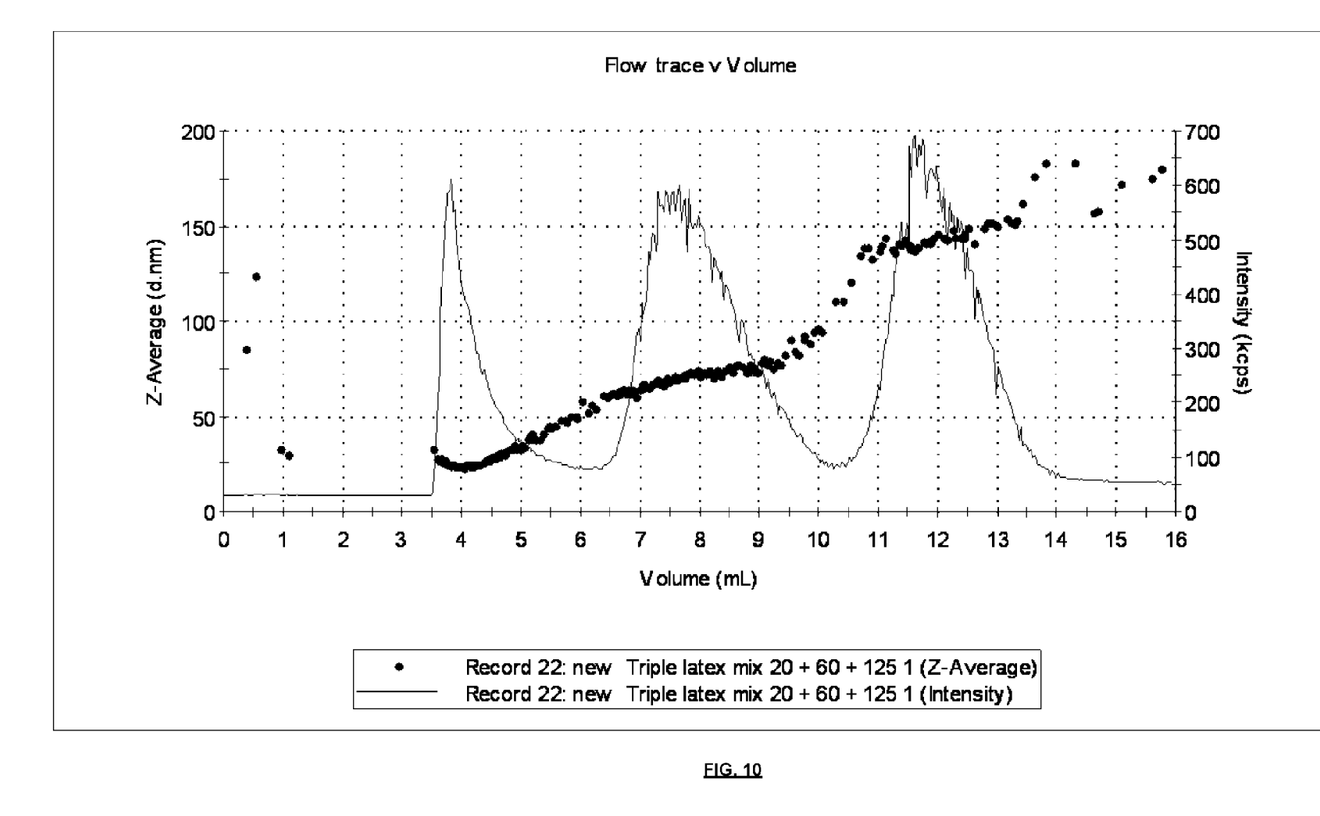
FIG. 10 is a plot that shows z-average and intensity data plotted against volume for a mix of three sizes of latex particles.

This right angle force tends to propel the sample particles to the bottom of the channel: in the case of XF4 this is effected by making the bottom of a membrane through which the solvent supporting the particles can penetrate, leaving the latter in the channel chamber itself. This tendency for particles to reside near the wall is countered by the natural Brownian motion (diffusion) of the particles and more readily in the case of the smaller sizes: hence as the suspension flows along the channel the smaller particles are less hindered by interaction with the membrane (wall) and tend to emerge (elute) before the larger ones. In practice, for a channel of a few centimeters in length, with a flow rate of 0.5 ml/minute, a sample of size 20 nanometers (nm) may emerge after ~8 minutes while one of 100 nm may emerge after 20 minutes. An example of the elution of a trimodal mixture is shown in FIG. 7. The green (unbroken) trace plots the intensity of light scattered as a function of time or elution volume: the two are considered commensurate since the fluid is pumped at a constant rate. In parallel, a continuous measurement of size is performed using dynamic light scattering to record the z-average hydrodynamic diameter. If the sample composition is known, or only relative measurements are required, such an absolute detection method may not be needed, but it can be a valuable diagnostic.

SUMMARY OF THE INVENTION

In one general aspect, the invention features an instrument for measuring characteristics of particles suspended in a fluid that includes a closed wall surface defining a fractionation channel having a input opening, an output opening, and a flow axis that spans downstream from the input opening for the channel to the output opening. A force application subsystem has a force application output oriented perpendicular to at least part of the flow axis of the fractionation channel. A particle characteristic measurement subsystem is located hydraulically downstream from at least a portion of the closed wall surface defining the fractionation channel, and includes a sensor positioned to sense a property of the suspended particles in the potential measurement subsystem as well as a signal output responsive to the sensor. A result processor has a signal input responsive to the signal output of the particle characteristic measurement subsystem, zeta potential processing logic responsive to the particle characteristic measurement subsystem, and a particle characteristic signal output responsive to the particle characteristic processing logic.

In preferred embodiments, the sensor can include a photon-counting detector with the particle characteristic measurement subsystem being configured to measure the particle characteristic based on light scattered by the particles. The instrument can further include a closed wall surface defining a sample injection channel hydraulically connected to a portion of the closed wall surface defining the fractionation channel upstream of the sensor, and further include a pump having an input responsive to a source of carrier fluid and an output hydraulically connected to the input opening of the closed wall surface defining the fractionation channel. The instrument can further include a common system controller having control outputs operatively connected to inputs of the pump and the particle characteristic measurement subsystem. The force application subsystem can be hydraulic. The force application subsystem can include a pump. The instrument can further include a display having an input operatively connected to the particle characteristic signal output to display an indication related to the particle characteristic measured by the particle characteristic measurement subsystem. The instrument can further include a time reference with the result processor being responsive to the particle characteristic measurement subsystem and to the time reference and being operative to provide an output signal on its particle characteristic signal output that is indicative of changes in particle characteristics over time. The result processor can also include particle size processing logic. The particle characteristic measurement subsystem can include a separate measurement cell hydraulically connected to the output opening of the closed wall surface defining the fractionation channel.

In another general aspect, the invention features a method for measuring characteristics of particles suspended in a fluid that includes receiving a fluid sample that includes a mix of suspended particles of different sizes, separating the differently sized particles in the fluid sample into a series of different fractions that include particles of different sizes, successively sensing at least one property of the particles in each fraction, and deriving different zeta potential values for the different fractions from results of the step of sensing.

In preferred embodiments, the step of receiving can receive a sample carried by a carrier fluid. The method can further include the step of displaying the different zeta potential values to an operator of the instrument. The method can further include the step of deriving different size values for different fractions.

In a further general aspect, the invention features an instrument for measuring characteristics of particles suspended in a fluid that includes means for receiving a fluid sample that includes suspended particles of different sizes, means for fractionating the fluid sample into a series of different fractions that include particles of different sizes, means for sensing properties of suspended particles in the fractions, and means responsive to the means for sensing for deriving different zeta potential values for the different fractions.

In another general aspect, systems according to the invention apply a zeta potential measurement to the eluting sample as well as, or instead of, a size measurement. This can be done in a suitable measurement cell where the electrophoretic separation is itself at right angles to the main flow and a suitable detector is arranged to measure the velocity achieved by the particles in this electric field. Some methods for doing this measurement on stationary particles are described in U.S. Pat. No. 7,217,350, granted May 15 2007, entitled "Mobility and Effects Arising from Surface Charge," issued to F. K. McNeil-Watson and M. T. Connah, and herein incorporated by reference. It is not essential and probably not convenient to do these measurements in the channel itself. The measurement cell can be connected by a fine tube to the output of the separation channel. Since particle diffusion is slow—microns per second or less—it is possible to measure the separated particles some time after leaving the separation channel without significant remixing. It is in fact more important to use a small measurement cell to avoid undue mixing.

Providing the electric field is applied across the flow direction the flow itself does not preclude making accurate velocity measurements in the field direction, particularly if an AC waveform and synchronous detection of particle movement to the waveform are used. This is implicit in the approach known as PALS (Phase Analysis Light Scattering) which can track small changes in particle movement. However general laser Doppler methods and other types of micro-electophoresis measurement could also be applied in the context of this invention. For example, direct microscopy and automated image analysis have been used to track and measure particle displacement, and would benefit from the presentation of particles classified by size in a predictable way: by changing magnification or illumination for example.

An advantage we foresee in coupling a derivative of a size and zeta potential instrument to an FFF system will apply particularly to the measurement of zeta potential distribution where size distribution and heterogeneity of particles is present. Zeta potential, while important in governing interparticle interaction and hence stability, is constrained in a fairly narrow range. Brownian motion also adds to the small micro-electrophoretic motion so small particles show a broad 'zeta potential distribution' even when the actual zeta value is identical for the entire population. Hence separating small and large particles before measuring zeta potential can reduce this loss of resolution.

DETAILED DESCRIPTION OF AN ILLUSTRATIVE EMBODIMENT

Figure 1:
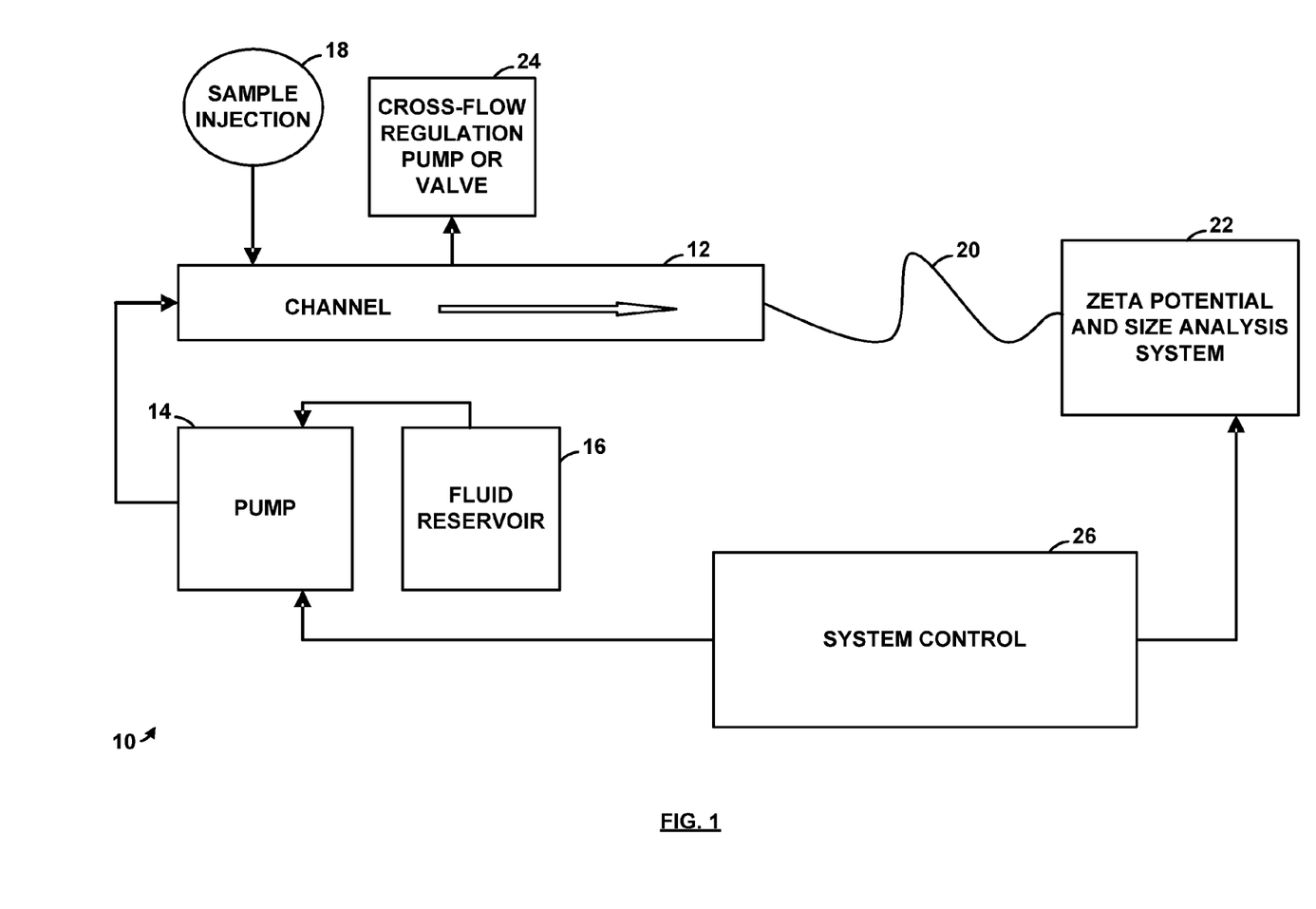
FIG. 1 is a block diagram of an illustrative particle characterization system according to the invention.

Referring to FIG. 1, an illustrative particle characterization system 10 according to the invention includes a channel 12 fed by a pump 14 from a fluid reservoir 16. A sample injection port 18 is provided at an upstream end of the channel and a connection 20, such as tubing, is provided between a downstream end of the channel and a Zeta potential and size analysis system 22. A cross-flow regulation pump or valve 24 can also be provided in the channel. A system controller 26 can be connected to control the pump and to the Zeta potential and size analysis system.

Figure 2:
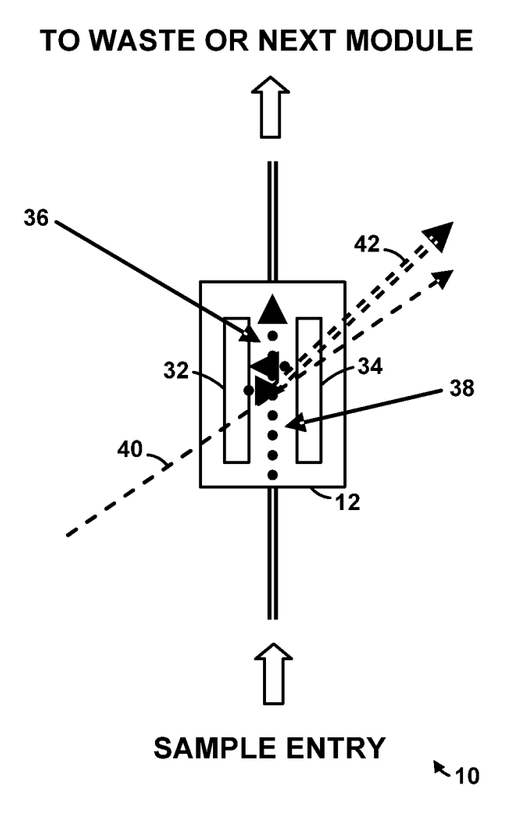
FIG. 2 is an illustrative schematic diagram of an illustrative electrophoresis cell for use with the illustrative particle characterization system of FIG. 1 (the FFF flow is perpendicular to the plane of the diagram)
Figure 3:
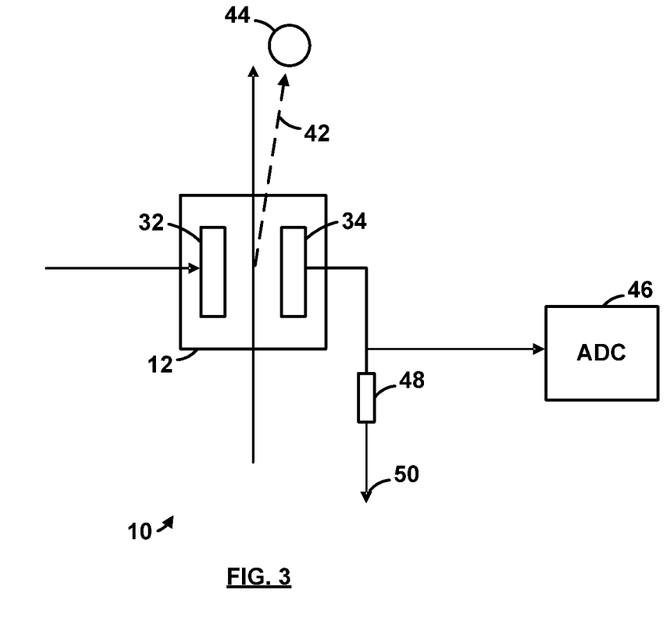
FIG. 3 is a schematic top view for the electrophoresis cell of FIG. 2.

Referring to FIGS. 2-3, an illustrative electrophoresis cell 30 for use with the illustrative particle characterization system of FIG. 1 includes a first electrode 32 and a second electrode 34 provided within the cell. Electrophoretic motion of particles 36 takes place between the electrodes and is normal to the flow 38 in the cell. An incident/illuminating laser beam 40 shines normal to both the sample flow and the electrophoretic motion. The resulting scattered light 42 is detected using scattered light collection optics 44 at around 12 degrees to the incident laser beam. Current flowing through the sample can be detected using an Analog-to-Digital Converted (ADC) 46 across a series resistor 48 connected between one of the electrodes and a ground or return terminal 50.

Referring to FIGS. 4-10, a model separation system will now be discussed. Most mineral samples in water-based suspensions will have zeta potentials in the range −100 to 100 millivolts, and at a certain pH many substances will have rather similar values. For example, a sample from a natural aquifer may contain mineral particles such as silicates, microbial matter, virus particles. All of these are likely to have zeta potentials in the range −20 to −50 mV in typical conditions (pH around 6-7, salt concentration around 1-10 mM equivalent). However, classifying by both size and zeta potential will lead to an enhanced ability to distinguish changes in such dispersions.

Figure 6:
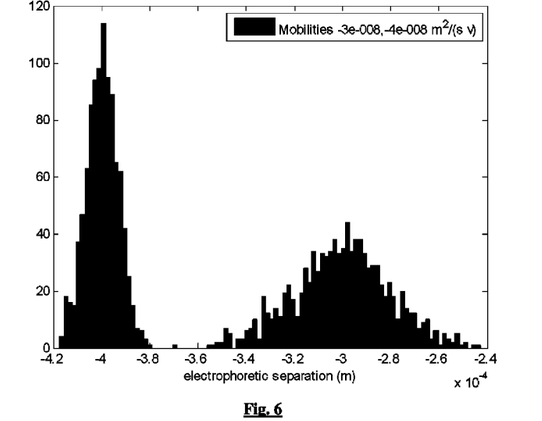
FIG. 6 is an illustrative mobility histogram for the model separation system ($\mu$E-4.0 and $-3.0\times10^{-8}$ m2/s/v for 100 nm)

In FIGS. 4 to 10 some examples are shown of a model separation system in which the zeta potential (Mobility) and size classification are performed simultaneously and presented as a two-dimensional map indicating where the sub populations reside after a certain period. Projections onto the individual axes show the output that either a size or zeta potential analyser on its own would find. FIGS. 3 and 6 show two different cases where different sized particle populations could either be distinguished or not depending on the size classification being performed. In FIG. 3 the mobility is different enough to show as a separate peak in the zeta potential/mobility histogram, where it is not (as in FIG. 6) the zeta analysis alone could not distinguish spread caused by true differences in zeta from the natural broadening due to Brownian motion.

Figure 4:
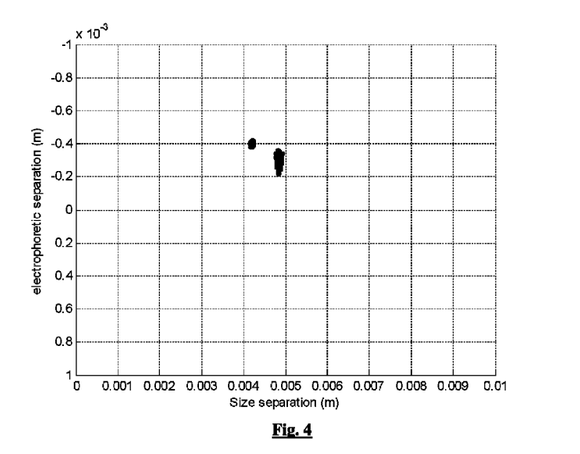
FIG. 4 is an illustrative plot of mobility against size for a model separation system according to the invention.
Figure 5:
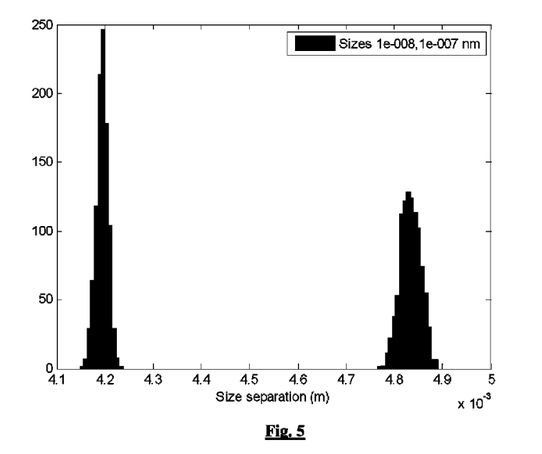
FIG. 5 is an illustrative size separation histogram for the model system separation system according invention.

FIG. 1 shows an overall view of the system which consists of a cross flow FFF apparatus connected to a light scattering instrument such as the Malvern Zetasizer capable of particle characterisation by both static and dynamic light scattering, and of zeta potential analysis using electrophoretic light scattering. One implementation of the measurement principle is shown in FIG. 2. A parallel plate electrode arrangement creates the elctrophoretic movement normal to the direction of flow. The illuminating beam passes through the cell normal to both the electric field and flow direction. The scattered light collected at around 12 degrees scattering angle as an example. Other scattering angles close to 0 or backscatter closer to 180 degrees are possible. A top view of the cell arrangement is shown in FIG. 3. When the field is applied the scattered light contains the spectral characteristics of electrophoretic and Brownian motion superimposed: when the field is off only Brownian motion is sensed. Hence it is possible to interleave the measurement of zeta potential (mobility) and particle size in a continuous series of coupled measurements while the eluting sample passes through. Hence the simultaneous presentation of size and mobility is possible as shown in FIGS. 4 and 7. Analysis and control can be performed by dedicated hardware and/or special-purpose software running on general-purpose computer hardware.

Although the arrangement illustrated is preferred it is not unique. The use of AC fields for the electrophoretic measurement as described in U.S. Pat. No. 7,217,350 will allow the detection of electrophoretic motion superimposed on a steady flow so the normal arrangement of the flow and detection axes shown here is not essential. The cell could be in the form of a capillary for example, with electrodes at either end.

The present invention has now been described in connection with a number of specific embodiments thereof. However, numerous modifications which are contemplated as falling within the scope of the present invention should now be apparent to those skilled in the art. Therefore, it is intended that the scope of the present invention be limited only by the scope of the claims appended hereto. In addition, the order of presentation of the claims should not be construed to limit the scope of any particular term in the claims.

What is claimed is:

1. An instrument for measuring characteristics of particles suspended in a fluid, comprising:
    a closed wall surface defining a fractionation channel having a input opening, an output opening, and a flow axis that spans downstream from the input opening for the channel to the output opening,
    a force application subsystem having a force application output oriented perpendicular to at least part of the flow axis of the fractionation channel,
    a particle characteristic measurement subsystem located hydraulically downstream from at least a portion of the closed wall surface defining the fractionation channel, and including a sensor positioned to sense a property of the suspended particles in the potential measurement subsystem as well as a signal output responsive to the sensor, and
    a result processor having a signal input responsive to the signal output of the particle characteristic measurement subsystem, zeta potential processing logic responsive to the particle characteristic measurement subsystem, and a particle characteristic signal output responsive to the particle characteristic processing logic.

2. The instrument of claim 1 wherein the sensor includes a photon-counting detector and wherein the particle characteristic measurement subsystem is configured to measure the particle characteristic based on light scattered by the particles.

3. The instrument of claim 1 further including a closed wall surface defining a sample injection channel hydraulically connected to a portion of the closed wall surface defining the fractionation channel upstream of the sensor, and further including a pump having an input responsive to a source of carrier fluid and an output hydraulically connected to the input opening of the closed wall surface defining the fractionation channel.

4. The instrument of claim 3 further including a common system controller having control outputs operatively connected to inputs of the pump and the particle characteristic measurement subsystem.

5. The instrument of claim 1 wherein the force application subsystem is hydraulic.

6. The instrument of claim 1 further including a display having an input operatively connected to the particle characteristic signal output to display an indication related to the particle characteristic measured by the particle characteristic measurement subsystem.

7. The instrument of claim 6 wherein the force application subsystem includes a pump.

8. The instrument of claim 1 further including a time reference and wherein the result processor is responsive to the particle characteristic measurement subsystem and to the time reference and is operative to provide an output signal on its particle characteristic signal output that is indicative of changes in particle characteristics over time.

9. The instrument of claim 1 wherein the result processor also includes particle size processing logic.

10. The instrument of claim 1 wherein the particle characteristic measurement subsystem includes a separate measurement cell hydraulically connected to the output opening of the closed wall surface defining the fractionation channel.

11. A method for measuring characteristics of particles suspended in a fluid, comprising:
    receiving a fluid sample that includes a mix of suspended particles of different sizes,
    separating the differently sized particles in the fluid sample into a series of different fractions that include particles of different sizes,
    successively sensing at least one property of the particles in each fraction, and
    deriving different zeta potential values for the different fractions from results of the step of sensing.

12. The method of claim 11 wherein the step of receiving receives a sample carried by a carrier fluid.

13. The method of claim 11 further including the step of displaying the different zeta potential values to an operator of the instrument.

14. The method of claim 11 further including the step of deriving different size values for different fractions.

15. An instrument for measuring characteristics of particles suspended in a fluid, comprising:
    means for receiving a fluid sample that includes suspended particles of different sizes,
    means for fractionating the fluid sample into a series of different fractions that include particles of different sizes,
    means for sensing properties of suspended particles in the fractions, and means responsive to the means for sensing for deriving different zeta potential values for the different fractions.

\* \* \* \* \*